United States Patent
Chu

(10) Patent No.: US 9,492,164 B2
(45) Date of Patent: *Nov. 15, 2016

(54) PLACING SUTURES

(71) Applicant: BOSTON SCIENTIFIC SCIMED, INC., Maple Grove, MN (US)

(72) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 478 days.

This patent is subject to a terminal disclaimer.

(21) Appl. No.: 13/734,111

(22) Filed: Jan. 4, 2013

(65) Prior Publication Data

US 2013/0123814 A1 May 16, 2013

Related U.S. Application Data

(63) Continuation of application No. 12/902,676, filed on Oct. 12, 2010, now Pat. No. 8,366,725, which is a
(Continued)

(51) Int. Cl.
*A61B 17/04* (2006.01)
*A61B 17/06* (2006.01)
*A61B 17/29* (2006.01)

(52) U.S. Cl.
CPC ....... *A61B 17/0491* (2013.01); *A61B 17/0469* (2013.01); *A61B 17/0482* (2013.01);
(Continued)

(58) Field of Classification Search
CPC ............ A61B 17/0469; A61B 17/0482; A61B 17/0491; A61B 17/0472; A61B 2017/06028; A61B 2017/2927
See application file for complete search history.

(56) References Cited

U.S. PATENT DOCUMENTS 342,773 A 6/1886 Bailey
919,138 A 4/1909 Drake et al.
(Continued)

FOREIGN PATENT DOCUMENTS

EP 0140557 A2 5/1985
EP 0689409 A1 3/1994
(Continued)

OTHER PUBLICATIONS

Lecture "Human Gross Anatomy and Embryology Pelvic Organs and Pelvic Diaphragm," by Dr. Roberts, University of Minnesota Medical School. Lecture given Fall 2000. Information posted to the internet before Oct. 17, 2000. Describes pelvic floor area.
(Continued)

*Primary Examiner* — Julian W Woo
(74) *Attorney, Agent, or Firm* — Brake Hughes Bellermann LLP

(57) ABSTRACT

A suturing instrument including multiple needle and suture assemblies that are at least partially disposed within the suturing instrument allows a surgeon to place multiple sutures intercorporally without having to remove the instrument from a surgical site and reload the instrument between placing each suture. The suturing instrument includes an elongate body member that includes a distal portion defining an opening. The suturing instrument further includes a first needle disposed within the opening, a second needle disposed within the opening, and a needle deployment mechanism disposed at least partially within the elongate body member and connectable sequentially to the first needle and the second needle.

17 Claims, 14 Drawing Sheets

Related U.S. Application Data continuation of application No. 11/374,691, filed on Mar. 13, 2006, now Pat. No. 7,833,235, which is a continuation of application No. 10/210,984, filed on Aug. 2, 2002, now Pat. No. 7,041,111.

(52) U.S. Cl.
CPC ............ *A61B 2017/0472* (2013.01); *A61B 2017/06028* (2013.01); *A61B 2017/2927* (2013.01)

(56) References Cited

U.S. PATENT DOCUMENTS

| | | |
|---|---|---|
| 1,037,864 A | 9/1912 | Carlson |
| 1,449,087 A | 3/1923 | Bugbee |
| 1,815,725 A | 7/1931 | Pilling et al. |
| 1,822,330 A | 9/1931 | Ainslie |
| 2,577,240 A | 12/1951 | Findley |
| 2,679,192 A | 12/1951 | Kohl |
| 3,160,157 A | 12/1964 | Chisman |
| 3,470,875 A | 10/1969 | Johnson |
| 3,638,653 A | 2/1972 | Berry |
| 3,840,017 A | 10/1974 | Violante |
| 3,918,455 A | 11/1975 | Coplan |
| 3,946,740 A | 3/1976 | Bassett |
| 3,986,468 A | 10/1976 | Szostak et al. |
| 4,161,951 A | 7/1979 | Scanlan, Jr. |
| 4,164,225 A | 8/1979 | Johnson et al. |
| 4,224,947 A | 9/1980 | Fukuda |
| 4,235,177 A | 11/1980 | Arbuckle |
| 4,238,470 A | 12/1980 | Young |
| 4,244,372 A | 1/1981 | Kapitanov et al. |
| 3,013,559 A | 12/1981 | Thomas |
| 4,312,337 A | 1/1982 | Donohue |
| 4,345,601 A | 8/1982 | Fukuda |
| 4,442,964 A | 4/1984 | Becht |
| 4,452,157 A | 6/1984 | Cantada et al. |
| 4,493,323 A | 1/1985 | Albright et al. |
| 4,548,202 A | 10/1985 | Duncan |
| 4,557,265 A | 12/1985 | Andersson |
| 4,579,072 A | 4/1986 | Koike et al. |
| 4,596,249 A | 6/1986 | Freda et al. |
| 4,602,635 A | 7/1986 | Mulhollan et al. |
| 4,621,640 A | 11/1986 | Mulhollan et al. |
| 4,635,638 A | 1/1987 | Weintraub et al. |
| 4,724,840 A | 2/1988 | McVay et al. |
| 4,762,260 A | 8/1988 | Richards et al. |
| 4,781,190 A | 11/1988 | Lee |
| 4,890,615 A | 1/1990 | Caspari et al. |
| 4,898,155 A | 2/1990 | Ovil et al. |
| 4,899,746 A | 2/1990 | Brunk |
| 4,923,461 A | 5/1990 | Caspari et al. |
| 4,926,860 A | 5/1990 | Stice et al. |
| 4,935,027 A | 6/1990 | Yoon |
| 4,957,498 A | 9/1990 | Caspari et al. |
| 5,037,433 A | 8/1991 | Wilk et al. |
| 5,047,039 A | 9/1991 | Avant et al. |
| 5,067,957 A | 11/1991 | Jervis |
| 5,100,415 A | 3/1992 | Hayhurst |
| 5,100,418 A | 3/1992 | Yoon et al. |
| 5,100,421 A | 3/1992 | Christoudias |
| 5,100,498 A | 3/1992 | Takeuchi et al. |
| 5,188,636 A | 2/1993 | Fedotov |
| 5,224,948 A | 7/1993 | Abe et al. |
| 5,258,011 A | 11/1993 | Drews |
| 5,275,614 A | 1/1994 | Haber et al. |
| 5,281,237 A | 1/1994 | Gimpelson |
| 5,282,809 A | 2/1994 | Kammerer et al. |
| 5,306,281 A | 4/1994 | Beurrier |
| 5,308,353 A | 5/1994 | Beurrier |
| 5,320,632 A | 6/1994 | Heidmueller |
| 5,324,298 A | 6/1994 | Phillips et al. |
| 5,336,231 A | 8/1994 | Adair |
| 5,364,408 A | 11/1994 | Gordon |
| 5,364,409 A | 11/1994 | Kuwabara et al. |
| 5,374,275 A | 12/1994 | Bradley et al. |
| 5,387,221 A | 2/1995 | Bisgaard |
| 5,389,103 A | 2/1995 | Melzer et al. |
| 5,391,174 A | 2/1995 | Weston |
| 5,417,699 A | 5/1995 | Klein et al. |
| 5,417,700 A | 5/1995 | Egan |
| 5,423,833 A | 6/1995 | Zauza |
| 5,441,507 A | 8/1995 | Wilk |
| 5,454,823 A | 10/1995 | Richardson et al. |
| 5,458,609 A | 10/1995 | Gordon et al. |
| 5,468,251 A | 11/1995 | Buelna |
| 5,470,338 A | 11/1995 | Whitfield et al. |
| 5,474,568 A | 12/1995 | Scott |
| 5,527,321 A | 6/1996 | Hinchliffe |
| 5,540,704 A | 7/1996 | Gordon et al. |
| 5,540,705 A | 7/1996 | Meade et al. |
| 5,573,542 A | 11/1996 | Stevens |
| 5,575,800 A | 11/1996 | Gordon |
| 5,578,044 A | 11/1996 | Gordon et al. |
| 5,591,177 A | 1/1997 | Lehrer |
| 5,591,179 A | 1/1997 | Edelstein |
| 5,593,421 A | 1/1997 | Bauer |
| 5,613,974 A | 3/1997 | Andreas et al. |
| 5,618,290 A | 4/1997 | Toy et al. |
| 5,632,751 A | 5/1997 | Piraka |
| 5,662,663 A | 9/1997 | Shallman |
| 5,662,664 A | 9/1997 | Gordon et al. |
| 5,662,666 A | 9/1997 | Onuki et al. |
| 5,665,096 A | 9/1997 | Yoon |
| 5,690,653 A | 11/1997 | Richardson et al. |
| 5,700,272 A | 12/1997 | Gordon et al. |
| 5,700,273 A | 12/1997 | Buelna et al. |
| 5,713,910 A | 2/1998 | Gordon et al. |
| 5,741,277 A | 4/1998 | Gordon et al. |
| 5,741,279 A | 4/1998 | Gordon et al. |
| 5,755,727 A | 5/1998 | Kontos |
| 5,759,188 A | 6/1998 | Yoon |
| 5,779,718 A | 7/1998 | Green et al. |
| 5,782,845 A | 7/1998 | Shewchuk |
| 5,814,054 A | 9/1998 | Kortenbach et al. |
| 5,827,298 A | 10/1998 | Hart et al. |
| 5,836,956 A | 11/1998 | Buelna et al. |
| 5,843,001 A | 12/1998 | Goldenberg |
| 5,855,585 A | 1/1999 | Kontos |
| 5,860,992 A | 1/1999 | Daniel et al. |
| 5,902,311 A | 5/1999 | Andreas et al. |
| 5,908,428 A | 6/1999 | Scirica et al. |
| 5,919,199 A | 7/1999 | Mers Kelly et al. |
| 5,951,575 A | 9/1999 | Bolduc et al. |
| 5,964,782 A | 10/1999 | Lafontaine et al. |
| 5,976,159 A | 11/1999 | Bolduc et al. |
| 5,984,917 A | 11/1999 | Fleischman et al. |
| 5,993,464 A | 11/1999 | Knodel |
| 6,048,351 A | 4/2000 | Gordon et al. |
| 6,059,800 A | 5/2000 | Hart et al. |
| 6,071,289 A | 6/2000 | Stefanchik et al. |
| 6,117,144 A | 9/2000 | Nobles et al. |
| 6,245,079 B1 | 6/2001 | Nobles et al. |
| 6,955,643 B2 | 10/2005 | Gellman et al. |
| 7,041,111 B2 | 5/2006 | Chu |
| 7,442,198 B2 * | 10/2008 | Gellman ............ A61B 17/0469 606/139 |
| 7,833,235 B2 | 11/2010 | Chu |
| 8,366,725 B2 * | 2/2013 | Chu .......................... 606/144 |
| 2006/0195121 A1 | 8/2006 | Chu |
| 2011/0028999 A1 | 2/2011 | Chu |

FOREIGN PATENT DOCUMENTS

| | | |
|---|---|---|
| EP | 674875 A1 | 10/1995 |
| GB | 2268690 A | 1/1994 |
| WO | WO-90/03768 A1 | 4/1990 |
| WO | WO-92/12674 A1 | 8/1992 |
| WO | WO-93/01750 A1 | 2/1993 |
| WO | WO-94/05213 A1 | 3/1994 |
| WO | WO-94/13211 A1 | 6/1994 |
| WO | WO-96/09796 A2 | 4/1996 |

(56) References Cited

FOREIGN PATENT DOCUMENTS

| WO | WO-96/27331 A1 | 9/1996 |
| WO | WO-99/47050 A2 | 9/1999 |
| WO | WO-01/28432 A1 | 4/2001 |

OTHER PUBLICATIONS

GyneFlex™ Instructions: Female Pelvic Floor Muscles. Shows color diagrams of the pelvic floor area. Printed Feb. 7, 2003.
Abington Memorial Hospital, "Physicians/Plastic Surgery/Pelvic Floor Dysfunction." Printed Feb. 6, 2003. Describes what the pelvic area constitutes.

* cited by examiner

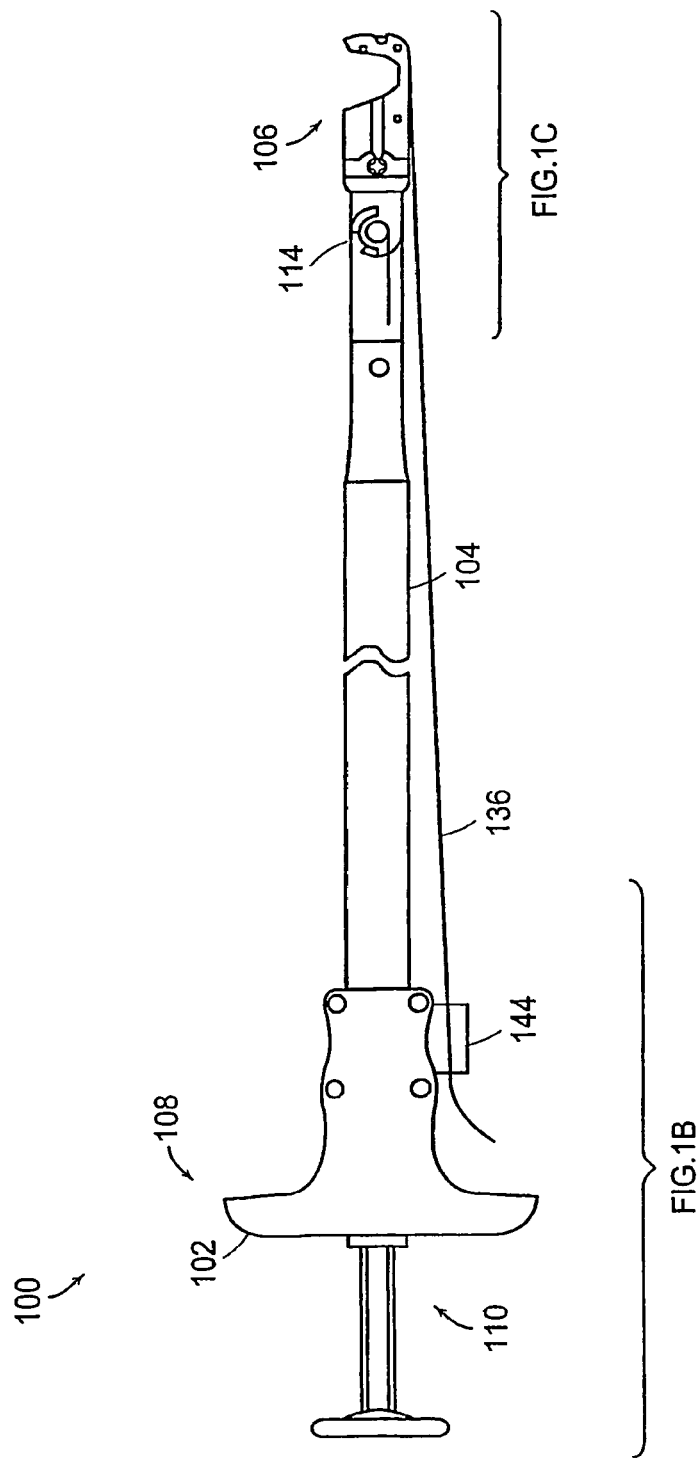

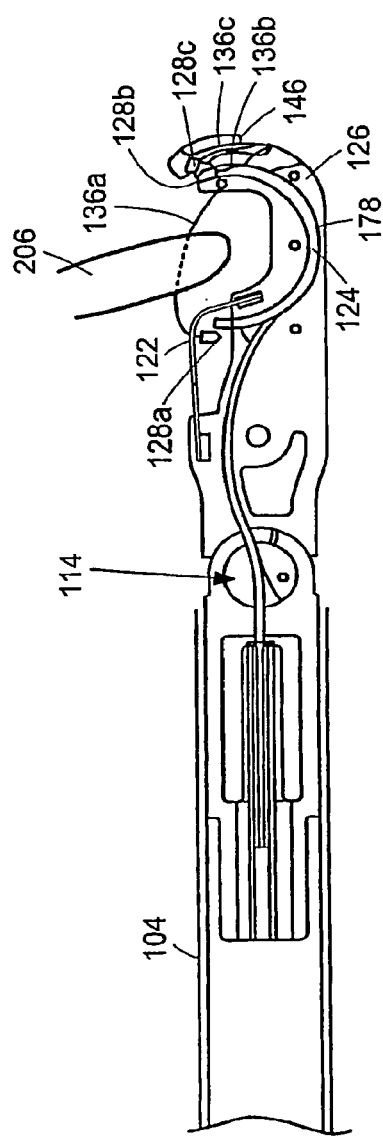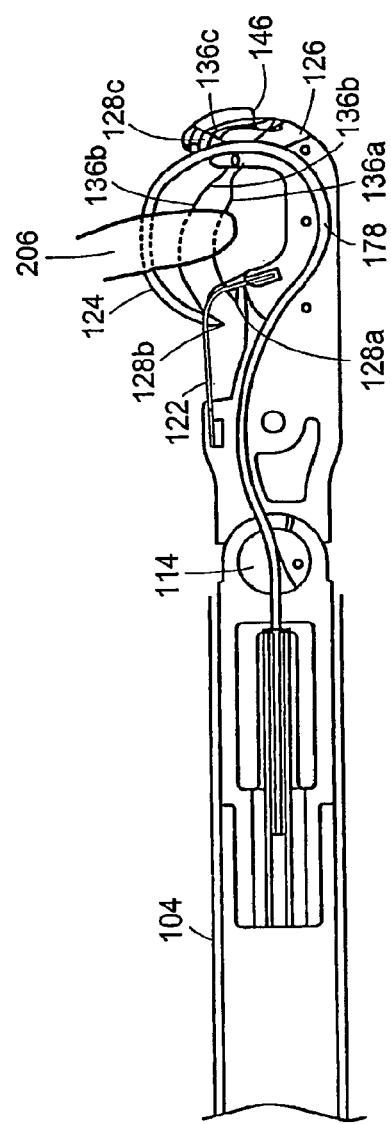
FIG. 4C
FIG. 4D

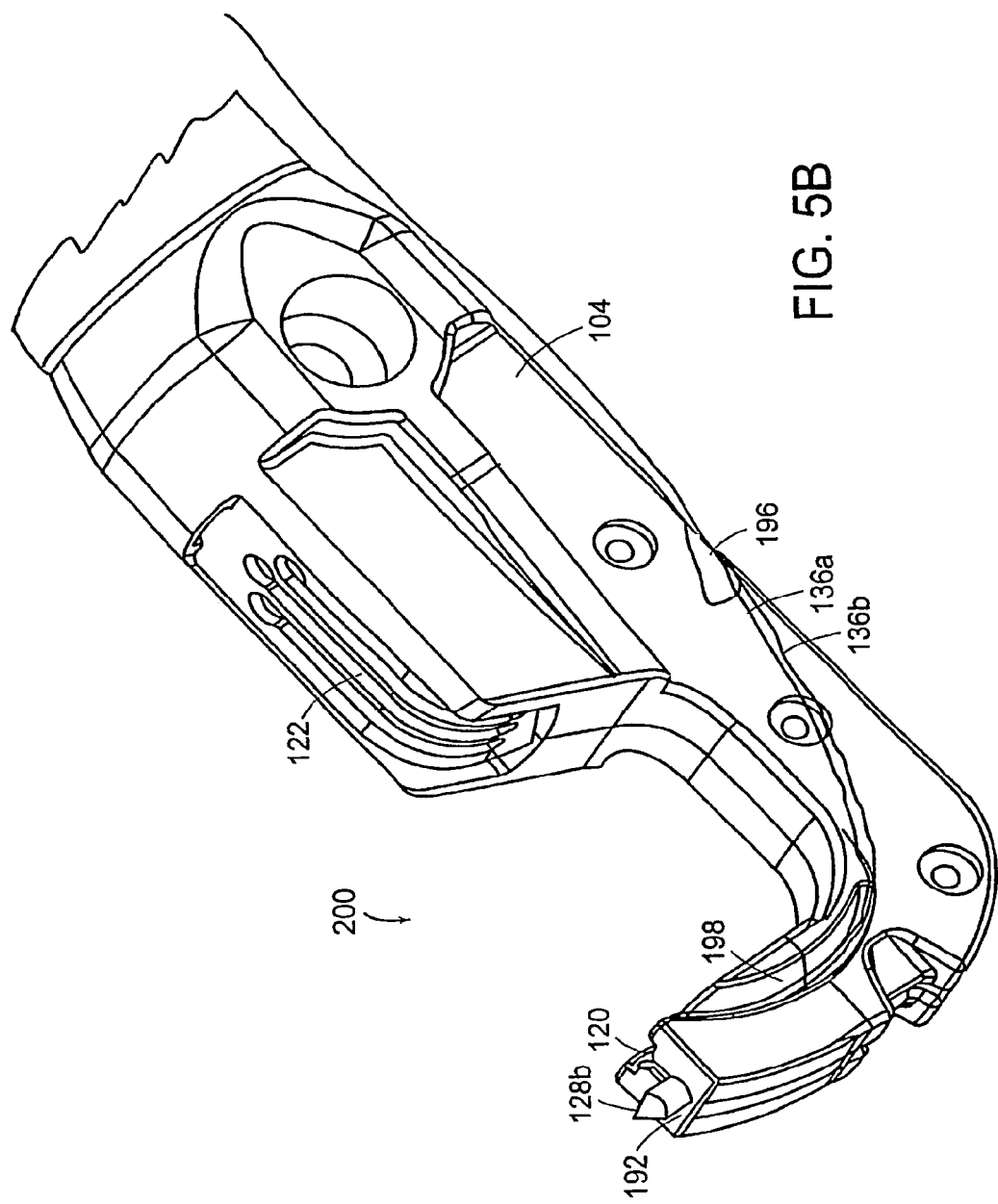

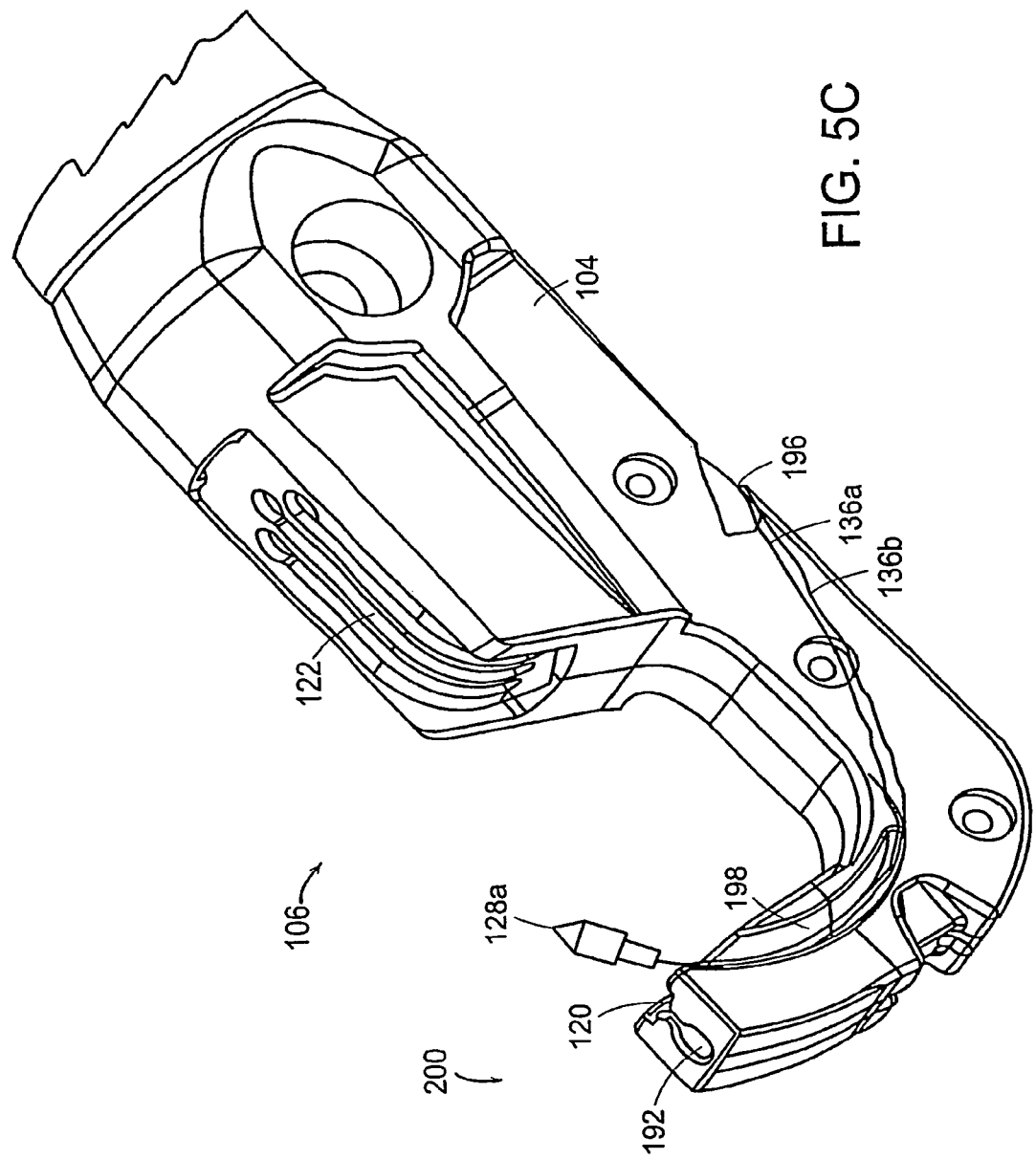

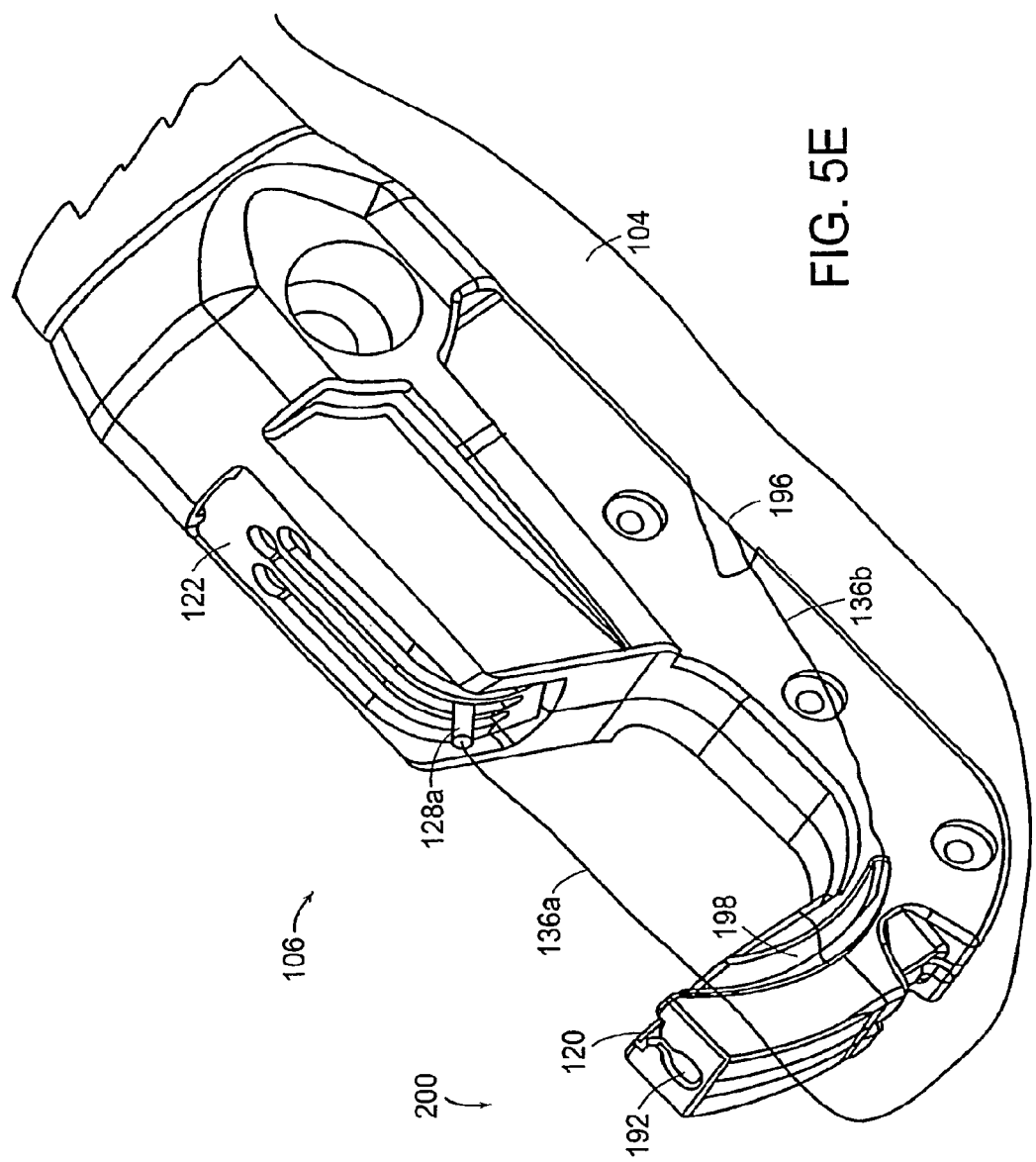

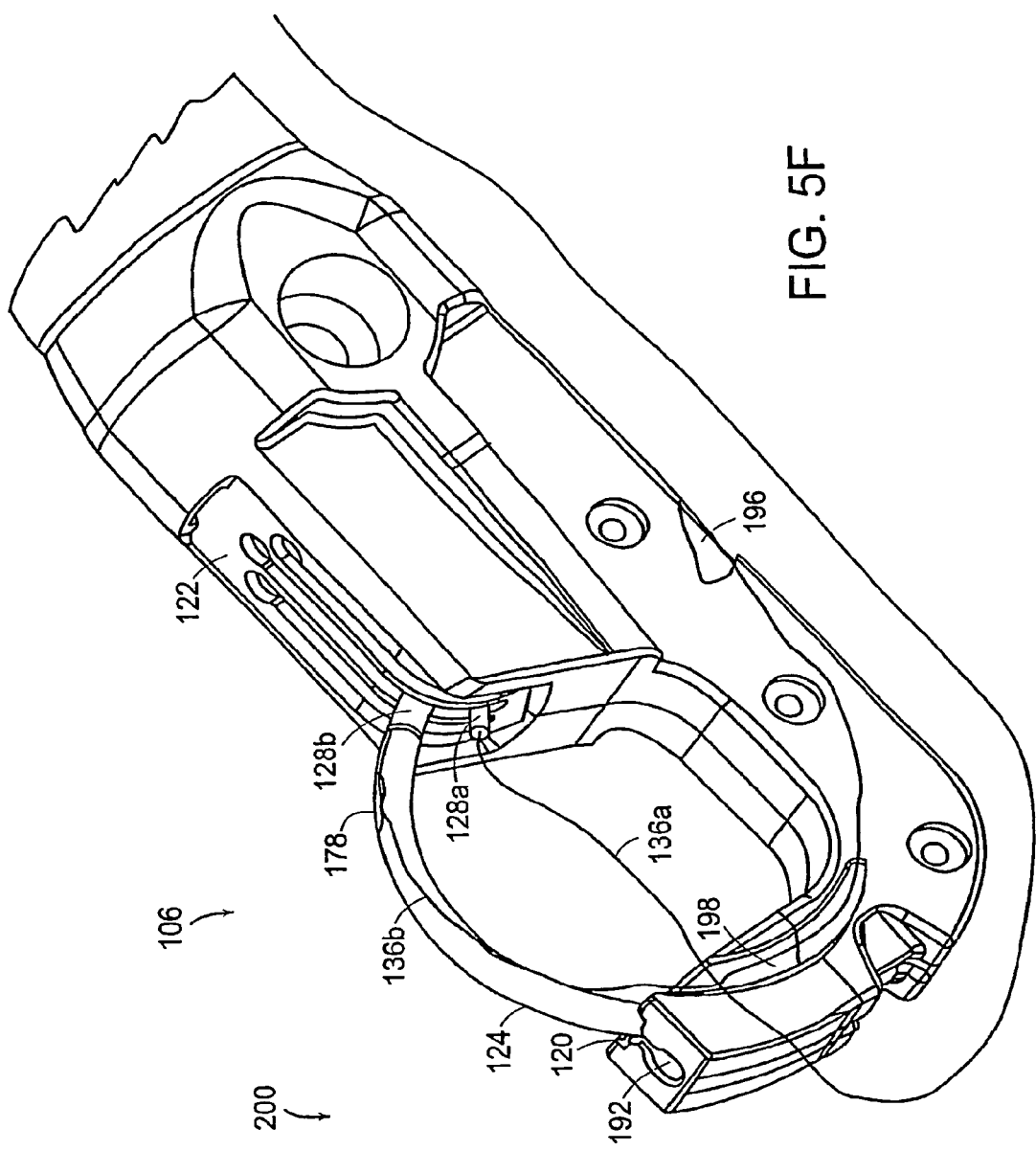

PLACING SUTURES

CROSS-REFERENCE TO RELATED CASES

This is a continuation of and claims the benefit of and priority to U.S. patent application Ser. No. 12/902,676 filed on Oct. 12, 2010, now U.S. Pat. No. 8,366,725, which is a continuation of U.S. patent application Ser. No. 11/374,691, filed on Mar. 13, 2006, now U.S. Pat. No. 7,833,235, which is a continuation of U.S. patent application Ser. No. 10/210,984, filed on Aug. 2, 2002, now U.S. Pat. No. 7,041,111. The entirety of each of these related cases is incorporated herein by reference.

TECHNICAL FIELD

The invention relates to devices and methods for placing sutures.

BACKGROUND INFORMATION

Suturing of body tissue is a time consuming aspect of many surgical procedures. For many surgical procedures, it is necessary to make a large opening in the human body to expose the area that requires surgical repair. There are instruments available that allow for viewing of certain areas of the human body through a small puncture wound without exposing the entire body cavity. These instruments, called endoscopes, can be used in conjunction with specialized surgical instruments to detect, diagnose, and repair areas of the body that previously required open surgery to access.

Some surgical instruments used in endoscopic procedures are limited by the manner in which they access the areas of the human body in need of repair. In particular, the instruments may not be able to access tissue or organs located deep within the body or that are in some way obstructed. Also, many of the instruments are limited by the way they grasp tissue, apply a suture, or recapture the needle and suture. Furthermore, many of the instruments are complicated and expensive to use due to the numerous parts and/or subassemblies required to make them function properly. Suturing remains a delicate and time-consuming aspect of most surgeries, including those performed endoscopically.

Many medical procedures require that multiple sutures be placed within a patient. Typical suturing instruments enable a surgeon to place only one suture at a time. With such suturing instruments, the surgeon is required to remove the instrument from a surgical site and reload the instrument between placing each suture. Further, the surgeon may be required to use forceps or other instruments to help place the suture. In some instances, the forceps or other instruments may require an additional incision to access the surgical site.

SUMMARY OF THE INVENTION

The invention generally relates to a suturing instrument that can house multiple needle and suture assemblies. The suturing instrument allows a surgeon to place multiple sutures without having to reload the instrument after each suture is placed, which is more efficient and less invasive than a procedure where the surgeon has to remove the instrument from the surgical site to reload. This is particularly helpful when the surgical site is located deep within a body and not easily repeatably accessible.

In one aspect, the invention is directed to a suturing instrument including an elongate body member, a first needle, a second needle, and a needle deployment mechanism. The elongate body member includes a distal portion that defines an opening. The first needle and the second needle are disposed within the opening. The needle deployment mechanism is at least partially disposed within the elongate body member and is connectable sequentially to the first needle and the second needle. The needle deployment mechanism moves the first needle and then the second needle out of the opening.

In various embodiments, the distal portion may further define a tunnel in communication with the opening. The tunnel may be disposed adjacent the opening, and the second needle and/or additional needles may be disposed within the tunnel. The suturing instrument may also include a needle catch disposed on the distal portion of the elongate body member. The needle catch is configured to receive the first needle and the second needle. The suturing instrument may also include a third needle disposed within the opening and connectable to the needle deployment mechanism. In one embodiment, the needle deployment mechanism includes a needle carrier and an actuator coupled to the needle carrier. The needle carrier may be disposed at least partially within the opening and the actuator may be disposed in a proximal portion of the elongate body member. The needle carrier may include a distal portion that defines a lumen for receiving at least one of the first needle and the second needle. The distal portion of the needle carrier may further define a slot in communication with the lumen for loading a suture.

In other embodiments, the second needle transitions from the opening to the lumen after the first needle is deployed from the elongate body member. The first needle and second needle may each include a distal portion and a suture attached thereto. The opening may include a bottom surface defining a slot for loading a suture. In additional embodiments, the elongate body member includes one or more bends. The suturing instrument can be adapted to access remote organs or tissue within a body. The distal portion of the elongate body member may be rotatable relative to a remainder of the elongate body member. Further, the suturing instrument may include a handle disposed opposite the distal portion of the elongate body member. The handle can at least partially house the needle deployment mechanism. The suturing instrument can be used, for example, to access areas within the patient's body to ligate, fixate, or approximate tissue.

These and other objects, along with advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 1A is a schematic plan view of one embodiment of a suturing instrument in accordance with the invention;

FIG. 4A-4E are partial schematic cross-sectional views of the distal portion of the suturing instrument of FIG. 1A during various operational phases;

FIG. 5B-5F are partial schematic perspective views of the distal portion of the suturing instrument of FIG. 5A.

DESCRIPTION

Figure 1B:
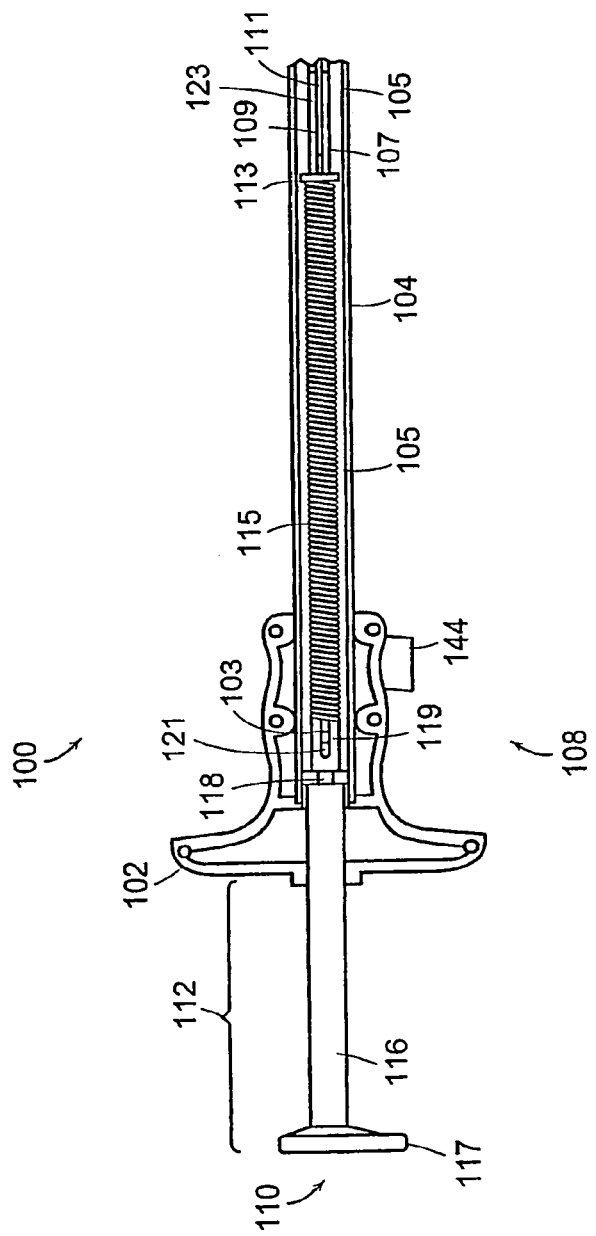
FIGS. 1B and 1C are schematic cross-sectional views of a proximal portion and a distal portion of the suturing instrument of FIG. 1A.

FIG. 1A depicts a suturing instrument 100 including a handle 102, an elongate body member 104, and a needle deployment mechanism 110. The suturing instrument 100 also includes a distal portion 106 and a proximal portion 108. The elongate body member 104 is mechanically coupled to the handle 102 at the proximal portion 108 and the suturing components are ate least partially disposed within the distal portion 106 of the suturing instrument 100.

Figure 3A:
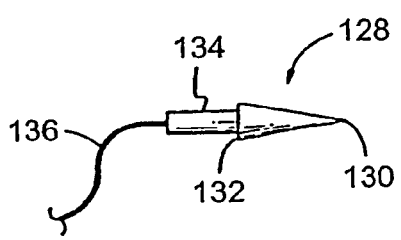
FIG. 3A is a schematic plan view of a needle coupled to a suture for use in a suturing instrument in accordance with the invention.

The handle 102 could take a variety of forms, for example, the handle 102 could be one of the types used with Boston Scientific Corporation suturing systems, in particular the Capio® Push & Catch suturing system. Generally, the needle deployment mechanism 110 extends longitudinally through the elongate body member 104 to the distal portion 106 of the suturing instrument 100, where the needle deployment mechanism 110 is coupled to a needle 128 (FIG. 3A). The needle deployment mechanism 110 moves the needle 128 between a retracted position and a deployed position. The needle deployment mechanism 110 is shown in greater detail in FIGS. 1B and 1C.

Referring to FIG. 1B, the proximal portion 108 of the suturing instrument 100 includes the handle 102, the elongate body member 104, a suture clip 144, and the needle deployment mechanism 110. The suture clip 144 may be coupled to the handle 102 or the elongate body member 104 and is used to hold an end of one or more sutures prior to placement in a patient. The needle deployment mechanism 110 includes an actuator 112 (button 117, shaft 116), a bearing 118, a button end 119, and a hole 121. The bearing 118 rides along a cylindrical surface 105 that is formed by the inside diameter of the elongate body member 104. A wireform 103 is inserted into the hole 121, coupling it to the actuator button 117. A spring 115 encircles the wireform 103, abuts the button end 119, and is compressed between the button end 119 and a spring washer 113. The spring washer 113 is seated upon a center tube 107. The center tube 107 is housed by the cylindrical surface 105 and is constrained in the distal portion 106. A pusher wire 111 is attached to the wireform 103 by means of a weld, a coupling, adhesive or other means, and is slidably disposed within a guidance sleeve 109, the sleeve 109 being disposed within a cylindrical surface 123 formed by the inside diameter of the center tube 107. In one embodiment, the pusher wire 111 is constructed of nitinol, so chosen for its combination of properties that allow for bendability and high column strength when constrained. Nitinol is a nickel-titanium alloy.

Figure 1C:
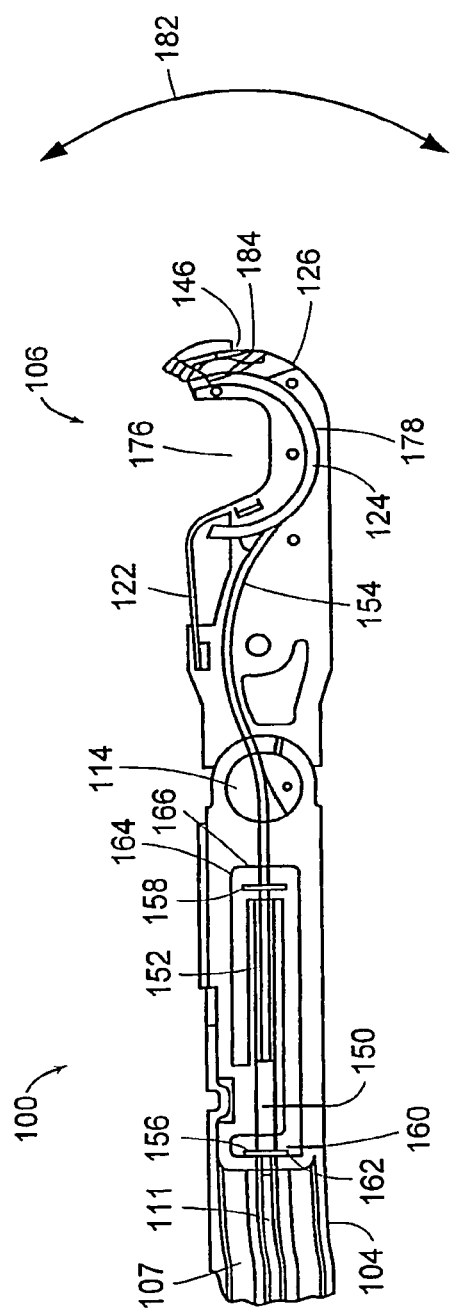

Referring to FIG. 1C, the distal portion 106 of the suturing instrument 100 of FIG. 1A includes the elongate body member 104, the needle deployment mechanism 110, an articulation mechanism 114, a curved portion 126, and a needle catch 122. Referring again to the needle deployment mechanism 110, the pusher wire 111 is attached by welding or other means to a coupling 150, which is slidably disposed within a track 152. The coupling 150 is attached to a carrier wire 154, which by virtue of its attachment to the coupling 150 is also slidably disposed within the track 152. The carrier wire 154 is mechanically coupled to an extendable needle carrier 124 by means of a weld, a coupling, adhesives, or other means. The coupling 150 abuts a backstop washer 156 that is slidably disposed about the pusher wire 111 and is contained within a pocket 160 that includes a back wall 162, against which the backstop washer 156 rests. The track 152 terminates distally in a pocket 164 that includes a wall 166. A downstop washer 158 is slidably disposed about the carrier wire 154 and constrained within the pocket 164.

In some embodiments, the suturing instrument 100 may include the articulation mechanism 114. The articulation mechanism 114 is disposed in the elongate body member 104 proximate the distal portion 106 (FIG. 1C). The articulation mechanism 114 facilitates the rotation (in the directions indicated by arrow 182) and positioning of the distal end 106 of the suturing instrument 100. In addition, the elongate body 104 can be substantially linear or may include one or more bends. The articulation mechanism 114 and/or bend(s) can facilitate access to deep and/or difficult to reach areas within the patient.

Figure 2A:
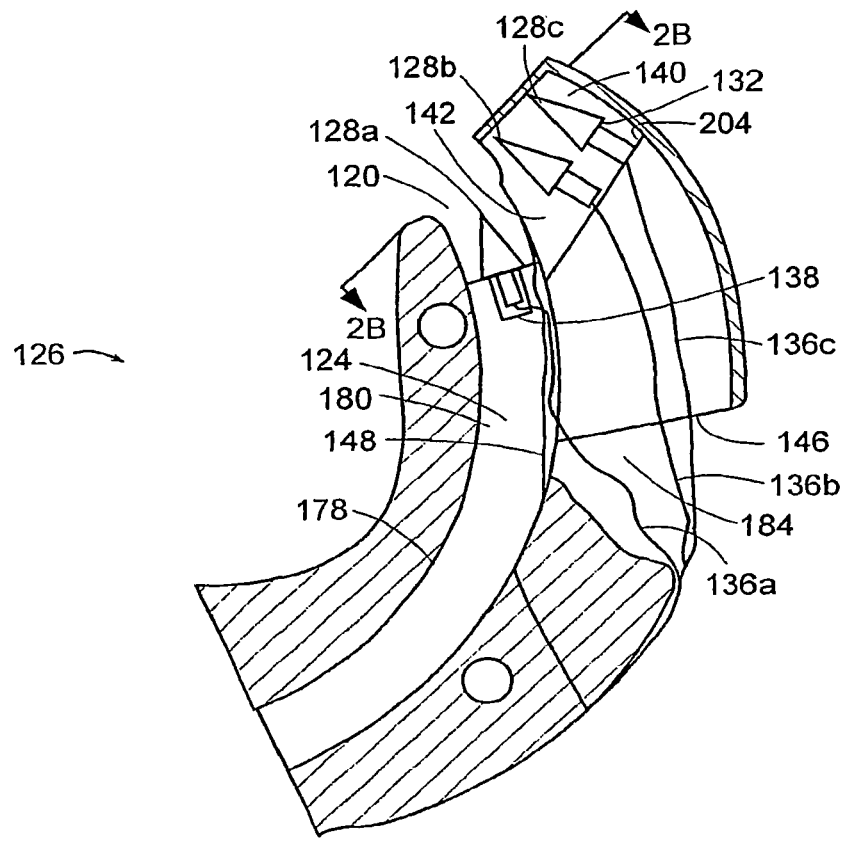
FIG. 2A is an enlarged cross-sectional view of the distal portion of the suturing instrument of FIG. 1A.
Figure 2B:
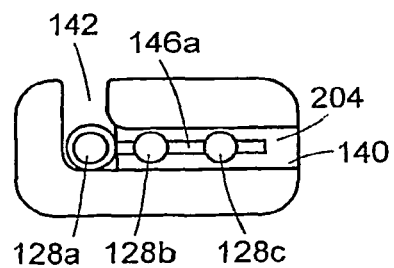
FIG. 2B is a schematic top view of the suturing instrument of FIG. 2A taken at line B-B.

Referring to FIGS. 2A and 2B, the curved portion 126 defines a channel 178, an opening (or needle exit port 120) including a tunnel or (needle compartment 140), a needle input/output slot 142, and a suture slot 146. The curved portion 126 also defines an opening 176 for receiving tissue (FIG. 1C). The curved portion 126 also includes a knot pusher 184. The needle carrier 124 is disposed within the channel 178 in the curved portion 126. A distal portion 180 of the needle carrier 124 defines a lumen 138 for holding a needle 128a, 128b, or 128c (generally needle 128).

Referring to FIG. 3A, in one embodiment, the needle 128 includes a tip 130 and a shaft 134 coupled to the tip 130, thereby forming a shoulder 132. The shaft 134 is coupled to a suture 136a, 136b, 136c (generally suture 136). The needle 128 is inserted into the lumen 138 and held by a slight friction fit. The suture 136 extends out of a needle carrier suture slot 148 and the suture slot 146. Needles 128b and 128c are stored in the needle compartment 140 prior to being deployed.

Figure 3B:
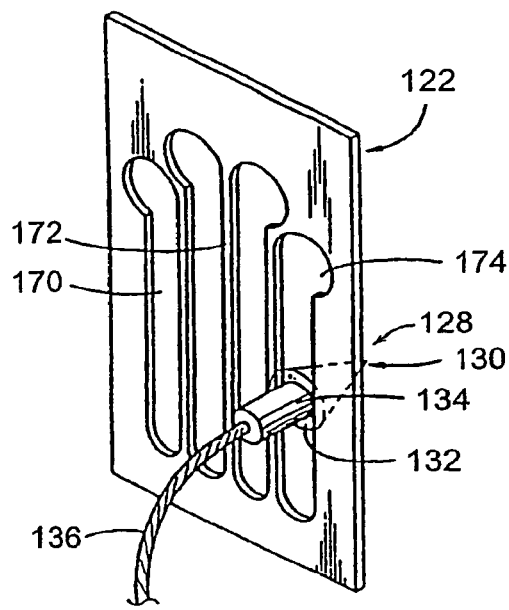
FIG. 3B is a schematic perspective view of a needle catch for use with the suturing instrument of FIG. 1A.

Referring again to FIGS. 1B, 1C, 2A, and 2B, in operation, a user (such as a physician or other medical personnel) actuates the needle deployment mechanism 110 by pushing on the button 117, which via the attachment to the wireform 103 which is attached to the pusher wire 111, moves the coupling 150 along the track 152 concomitantly moving the carrier wire 154, which slidably moves the needle carrier 124 through the needle exit port 120. The user continues to push the button 117 until the needle 128 enters the needle catch 122. The needle catch 122, as shown in FIG. 3B, includes openings 170 defined by successive ribs 172. The needle catch 122 receives the needle 128 (coupled to the suture 136) through opening 170, the ribs 172 deflect slightly to allow the needle 128 to pass through. After the formed shoulder 132 has passed the ribs 172, the ribs 172 spring back to their original position defining the openings 170, and the needle 128 remains captured in the needle catch 122. The user releases the button 117 and the spring 115 urges the button 117 proximally, moving the pusher wire 111, the coupling 150, the carrier wire 154, and the needle carrier 124 proximally along with the button 117 to the retracted position. As the needle carrier 124 moves back to the retracted position, the needle 128 slides out of the lumen 138. The openings 170 are chosen to be smaller in dimension than the formed shoulder 132. This causes the needle catch 122 to retain the needle 128 because the flat rear surface of the shoulder 132 prevents the needle 128 from passing back through the opening 170. When it is necessary to remove the needle 128 from the needle catch 122, the needle 128 may be moved toward an enlarged portion 174 of opening 172. The enlarged portion 174 is sized to allow the formed shoulder 132 to pass through without resistance. The needle catch 122 is preferably constructed of thin stainless steel of high temper, such as ANSI 301 full hard. The needle catch 122 may be fabricated by means of stamping, laser machining, or chemical etching.

The suturing instrument's component materials should be biocompatible. For example, the handle 102, the elongate body member 104, and portions of the needle deployment mechanism 110 may be fabricated from extruded, molded, or machined plastic material(s), such as polypropylene, polycarbonate, or glass-filled polycarbonate. Other components, for example the needle 128, may be made of stainless steel. Other suitable materials will be apparent to those skilled in the art. The material(s) used to form the suture should be biocompatible. The surgeon will select the length, diameter, and characteristics of the suture to suit a particular application. Additionally, the mechanical components and operation are similar in nature to those disclosed in U.S. Pat. Nos. 5,364,408 and 6,048,351, each of which is incorporated by reference herein in its entirety.

Referring to FIGS. 2A-2B and 4A-4E, the present invention enables a user to place multiple sutures 136 in a patient without removing the suturing instrument 100 from the patient. The user loads the suture 136c through the first suture slot 146a until the suture 136c emerges from the second suture slot 146b. The user then inserts the needle 128c through the needle input/output slot 142 into the needle compartment 140. The user repeats this process for additional sutures 136 and needles 128. The user can repeat this process for loading the first suture 136a and the first needle 128a, or the user can insert the first needle 128a directly into the needle carrier 124. In either case, the sutures 136a, 136b, 136c extend out of the second suture slot 146b. If the needle 128a is loaded into the needle compartment 140, the user pulls on the first suture 136a (held by the suture clip 144) to cause the first needle 128a to slide down an inclined needle shelf 204 and out of the needle compartment 140 through the needle output slot 142 into the lumen 138 of the needle carrier 124. The suture 136a extends out of the needle suture slot 148 and the second suture slot 146b.

In another embodiment, the suture 136a could be pulled by attaching the suture 136a to a spool mounted on the elongate body member 104 and winding the spool. In still other embodiments, the suture 136a could be pulled by other mechanical means known in the art, such as by a lever, for example. After the needles 128a, 128b, 128c and sutures 136a, 136b, 136c are loaded into the suturing instrument 100, portions of the sutures 136a, 136b, 136c extending out the suture slot 146b are held by the suture clip 144 (FIG. 1B). The needle carrier 124, which is part of the needle deployment mechanism 110, is sequentially connectable to the needles 128 stored in the needle compartment 140. This means that each needle 128 stored in the needle compartment 140 is connected to, and then deployed by, the needle carrier 124 one at a time in the order the needles 128 are dispensed from the needle compartment 140.

Figure 4A:
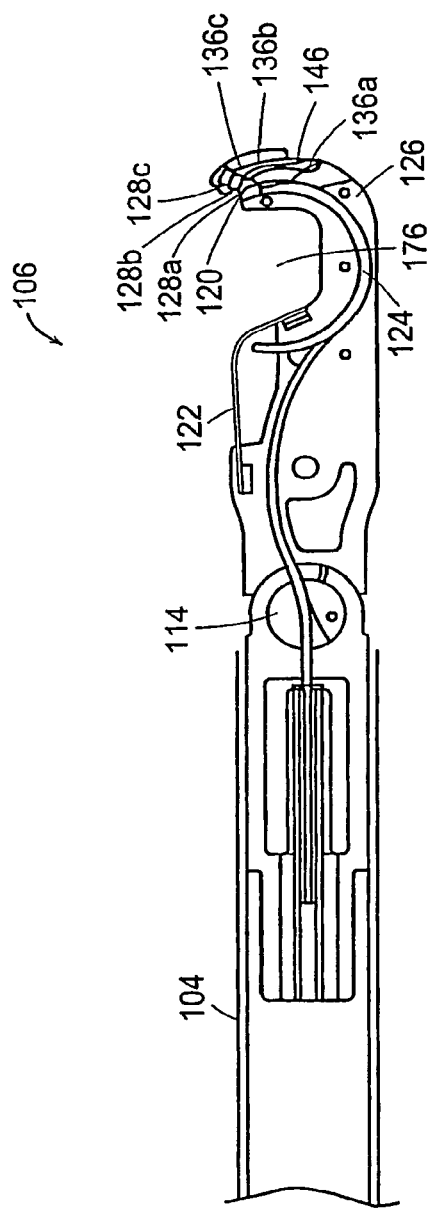
Figure 4B:
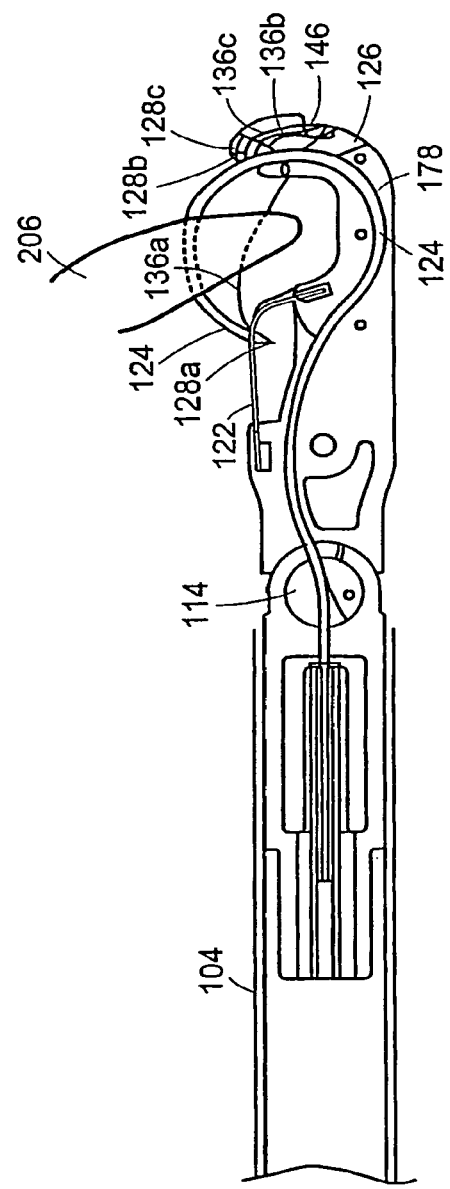

The user then inserts the elongate body member 104 into a patient and orients the elongate body member 104 so that the needle exit port 120 is proximate to or in contact with the tissue 206 to be sutured. The user then pushes the button 117 (FIG. 1B), as described above. Pushing the button 117 causes the needle carrier 124 (holding the first needle 128a) to extend out of the needle exit port 120 and push the needle 128a through the tissue 206. As the first needle 128a is pushed through the tissue 206, the first needle 128a pulls the first suture 136a through the tissue 206. As the user continues to push the button 117, the needle carrier 124 continues to advance out of the needle exit port 120 and directs the first needle 128a and the first suture 136a toward the needle catch 122. The user continues to push the button 117 until the first needle 128a contacts and becomes captured by the needle catch 122 (FIG. 4B). The user then retracts the needle carrier 124 by releasing the button 117, as previously described.

Figure 4E:
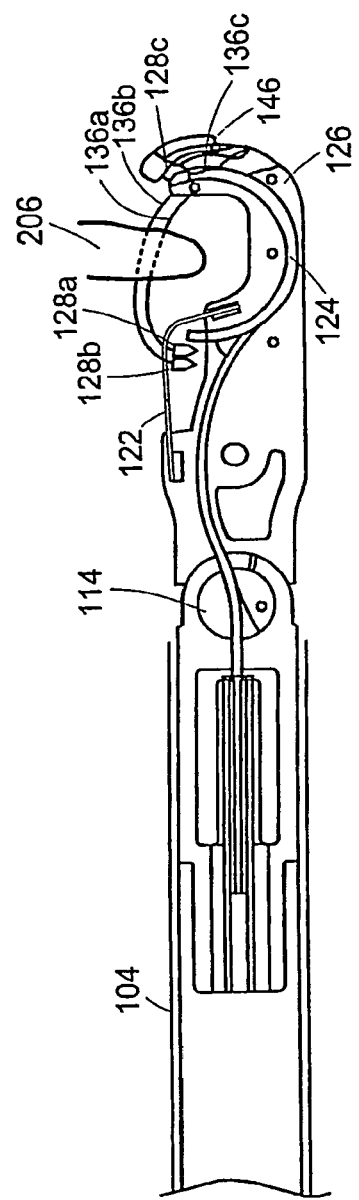

After the user retracts the needle carrier 124, the first needle 128a and the first suture 136a are left captured within the needle catch 122, with the first suture 136a extending through the tissue 206 (FIG. 4C). When the needle carrier 124 returns to a fully retracted position, the user pulls on the second suture 136b to cause the second needle 128b to slide down the inclined needle shelf 204 and out of the needle compartment 140 through the needle input/output slot 142 and into the lumen 138 of the needle carrier 124. The second suture 136b extends out of the needle carrier suture slot 148 and the second suture slot 146b. The user then advances the needle carrier 124 as described above until the second needle 128b is captured by the needle catch 122 (FIG. 4D). The user then retracts the needle carrier 124 as described above leaving the second needle 128b and the second suture 136b captured by the needle catch 122 (FIG. 4E). This procedure can be repeated for the third needle 128c, or for as many needles as may be stored in the needle compartment 140.

After one or more sutures 136 have been placed, the user withdraws the suturing instrument 100 from the patient. The user detaches the suture(s) 136 from the needle(s) 128 and ties a knot or knots into the suture(s) 136. The user can then use the knot pusher 184 to push the knot(s) into the patient as the knot(s) is tightened.

Figure 5A:
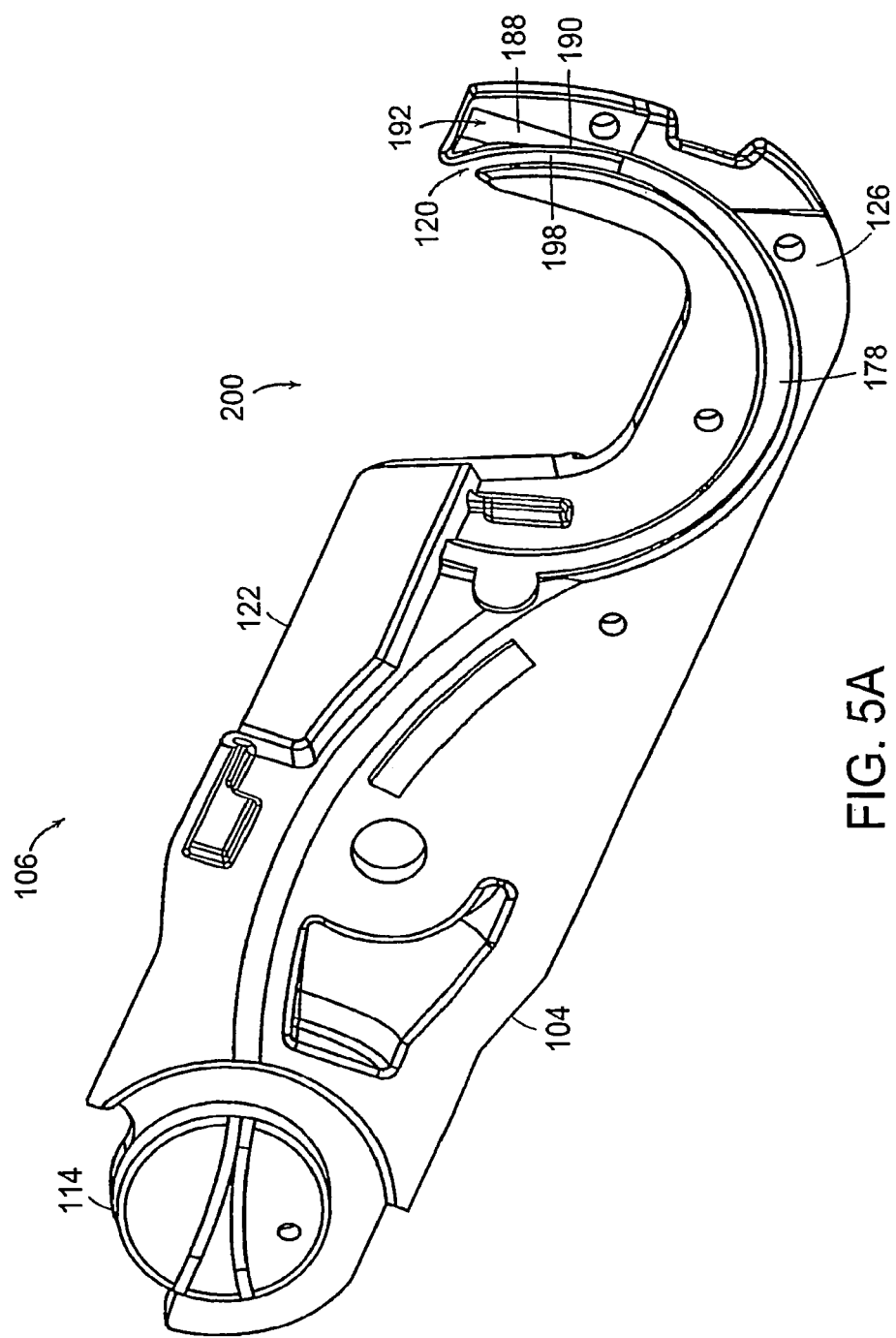
FIG. 5A is a partial schematic cross-sectional view of a distal portion of a suturing instrument in accordance with another embodiment of the invention.

Referring to FIGS. 5A-5F, in an alternative embodiment, the distal portion 106 of the suturing instrument 100 includes a curved portion 200. The curved portion 200 defines a needle compartment 188, a needle output slot 190, a needle loading slot 192, a first suture slot 196 (FIG. 5B), and a second suture slot 198. In this embodiment, a needle 128a is inserted into the needle carrier 124 with a suture 136a extending through the needle carrier suture slot 148, the first suture slot 196 and the second suture slot 198. An additional needle 128b is inserted into the needle compartment 188 through the needle loading slot 192 with a suture 136b-extending through the first suture slot 196 and the second suture slot 198 (FIG. 5B).

Figure 5D:
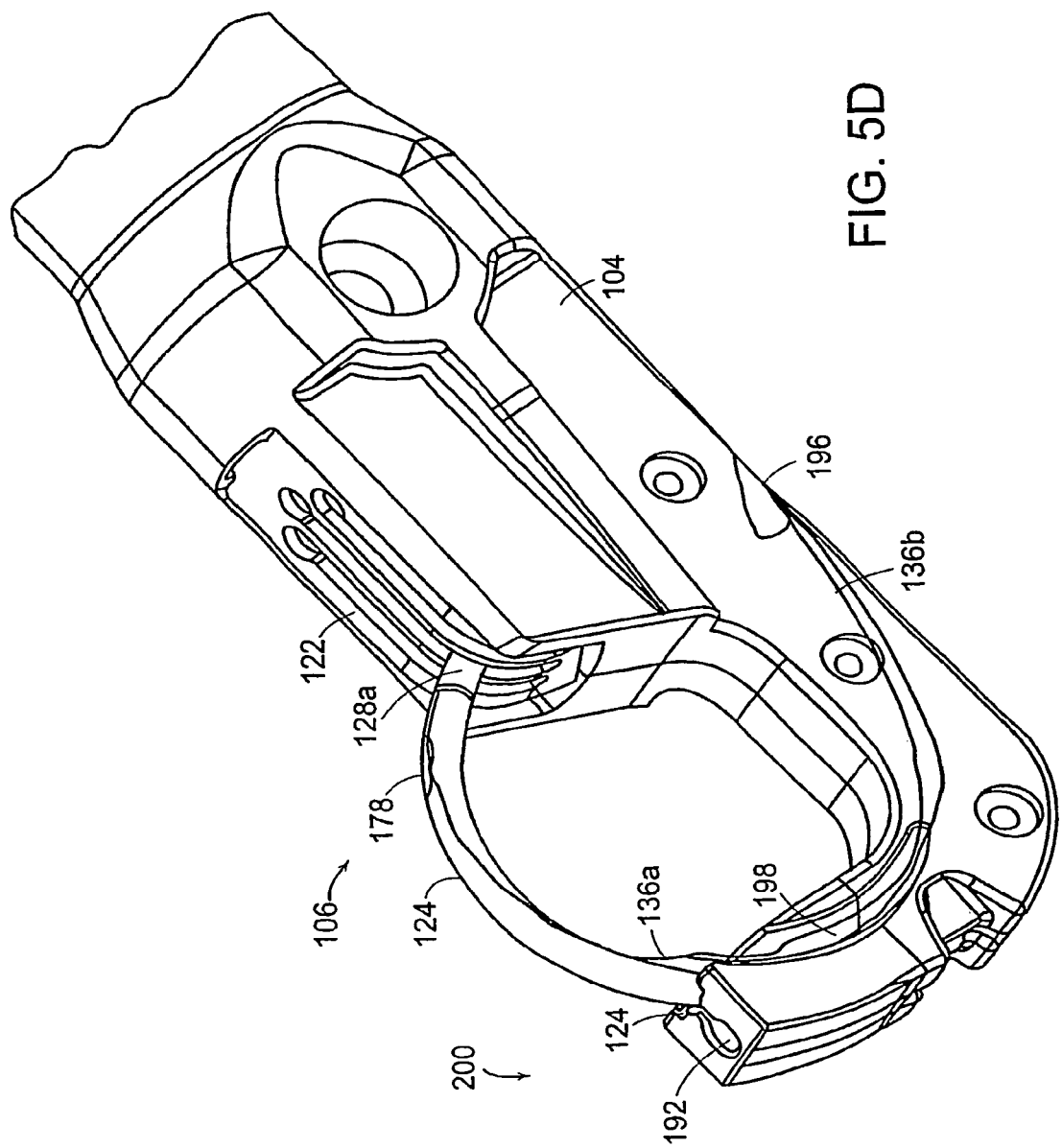

In operation, this alternative embodiment functions largely the same way as the embodiment previously described. The user advances the needle carrier 124 by pressing the button 117 (FIG. 1A) until the first needle 128a along with the first suture 136a is driven through the tissue and captured by the needle catch 122 (FIG. 5D). After the needle 128a and the suture 136a are captured in the needle catch 122, the needle carrier 124 is retracted so that the second needle 128b can be loaded into the needle carrier 124 (FIG. 5E). When the needle carrier 124 is fully retracted, the user pulls the second suture 136b causing the second needle 128b to slide into the needle carrier 124 from the needle compartment 188 through the needle loading slot 190. The user again advances the needle carrier 124 out of the needle exit port 120, through the tissue, and into the needle catch 122 (FIG. 5F). The user then retracts the needle carrier 124 leaving the needle 128b and coupled suture 136b captured by the needle catch 122. In other embodiments, more needles 128 and sutures 136 can be loaded into the needle compartment 188.

Other embodiments incorporating the concepts disclosed herein may be used without departing from the spirit and scope of the invention. The described embodiments are to be considered in all respects as only illustrative and not restrictive.

What is claimed is:

1. A suturing instrument comprising
an elongate body member including a distal portion defining an opening, the distal portion including a curved portion, the curved portion including a channel that extends to the opening and a needle compartment configured to store at least two needles, the needle compartment defining a side slot in which the at least two needles are sequentially deployed from the needle compartment to the channel, the needle compartment including a needle shelf, each of the at least two needles being coupled to a suture; and
a needle deployment mechanism disposed at least partially within the elongate body member and configured to sequentially deploy the at least two needles out of the opening,
the distal portion of the elongate body member being movable relative to a proximal portion of the elongate body member,
wherein each of the at least two needles is configured to slide down the needle shelf and out of the needle compartment based on a pulling force applied by a user on the suture.

2. The suturing instrument of claim 1 further comprising a handle disposed opposite to the distal portion of the elongate body member.

3. The suturing instrument of claim 1 wherein the elongate body member is adapted to access organs or tissue within a body of a patient.

4. The suturing instrument of claim 1 wherein the needle deployment mechanism includes a needle carrier configured to deploy the at least two needles out of the opening.

5. The suturing instrument of claim 4 wherein the needle carrier defines a lumen for sequentially receiving each of the at least two needles.

6. The suturing instrument of claim 4 wherein the needle carrier is configured to deploy the at least two needles out of the opening and in a proximal direction.

7. The suturing instrument of claim 1 wherein the distal portion further defines a needle catch.

8. The suturing instrument of claim 7 wherein the needle catch is configured to sequentially receive the at least two needles.

9. The suturing instrument of claim 1 further comprising the at least two needles loaded into the distal portion.

10. A suturing instrument comprising
an elongate body member defining an opening, the elongate body member including a distal portion having a curved portion, the curved portion including a channel that extends to the opening and a needle compartment configured to releasably hold at least two needles and a suture slot, the needle compartment defining a side slot in which the at least two needles are sequentially deployed from the needle compartment to the channel, the needle compartment including a needle shelf, each of the at least two needles being coupled to a suture; and
a needle deployment mechanism disposed at least partially within the elongate body member and configured to sequentially deploy the at least two needles out of the opening,
the distal portion of the elongate body member being movable relative to a proximal portion of the elongate body member,
wherein each of the at least two needles is configured to slide down the needle shelf and out of the needle compartment based on a pulling force applied by a user on the suture.

11. The suturing instrument of claim 10, wherein each of the at least two needles define a tip and a shaft coupled to the tip such that an intersection of the tip and the shaft define a shoulder.

12. The suturing instrument of claim 10 wherein the elongate body member further includes a needle catch.

13. The suturing instrument of claim 12 wherein the needle catch is located proximal relative to the needle compartment on the elongate body member.

14. The suturing instrument of claim 12 wherein the needle catch is configured to sequentially receive the at least two needles.

15. The suturing instrument of claim 10 further comprising the at least two needles loaded into the portion of the elongate body.

16. The suturing instrument of claim 10 wherein the needle deployment mechanism includes a needle carrier configured to deploy the at least two needles out of the opening.

17. The suturing instrument of claim 16 wherein the needle carrier defines a lumen for sequentially receiving each of the at least two needles.

* * * * *